US007008647B2

(12) United States Patent
Burrell et al.

(10) Patent No.: US 7,008,647 B2
(45) Date of Patent: *Mar. 7, 2006

(54) TREATMENT OF ACNE

(75) Inventors: Robert Edward Burrell, Sherwood Park (CA); Hua Qing Yin, Sherwood Park (CA)

(73) Assignee: Nucryst Pharmaceuticals Corp., Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/840,637

(22) Filed: Apr. 23, 2001

(65) Prior Publication Data
US 2002/0192298 A1 Dec. 19, 2002

(51) Int. Cl.
*A61K 9/14* (2006.01)
*A61K 9/08* (2006.01)
*A61K 33/00* (2006.01)
*A61K 33/24* (2006.01)
*A61K 33/38* (2006.01)

(52) U.S. Cl. ...................... 424/618; 424/400; 424/402; 424/404; 424/405; 424/409; 424/411; 424/443; 424/444; 424/445; 424/446; 424/447; 424/448; 424/489; 424/490; 424/600; 424/604; 424/617; 424/619; 424/630; 424/631; 424/632; 424/633; 424/634; 424/635; 424/637; 424/638; 424/641; 424/642; 424/643; 424/646; 424/649; 424/650; 424/651; 424/653; 424/682; 602/41; 514/492; 514/493; 514/494; 514/495; 514/499; 514/500; 514/503; 514/859; 514/886; 514/887; 514/944; 514/951; 514/952; 514/953; 514/964; 514/965

(58) Field of Classification Search .............. 514/859, 514/492–495, 499–500, 503, 886, 887, 944, 514/951, 952, 963, 964, 965; 424/617–619, 424/646, 649–651, 682, 489, 400, 402, 404, 424/405, 409, 411, 443–448, 490, 600, 604, 424/630–635, 637–638, 641–643, 653; 602/41
See application file for complete search history.

(56) References Cited

U.S. PATENT DOCUMENTS

| 3,757,786 A | 9/1973 | Smith |
| 3,800,792 A | 4/1974 | McKnight et al. .......... 128/156 |
| 3,918,446 A | 11/1975 | Buttaravoli |
| 4,059,105 A | 11/1977 | Citruzzula et al. |
| 4,324,237 A | 4/1982 | Buttaravoli |
| 4,355,636 A | 10/1982 | Oetjen et al. |
| 4,476,590 A | 10/1984 | Scales et al. |
| 4,581,028 A | 4/1986 | Fox, Jr. et al. |
| 4,596,556 A | 6/1986 | Morrow et al. |
| 4,633,863 A | 1/1987 | Filips et al. |
| 4,749,572 A | 6/1988 | Ahari ........................ 424/132 |
| 4,790,824 A | 12/1988 | Morrow et al. |
| 4,803,066 A | 2/1989 | Edwards ..................... 424/132 |
| 4,828,832 A | 5/1989 | De Cuellar et al. ......... 424/618 |
| 4,847,049 A | 7/1989 | Yamamoto |
| 4,952,411 A | 8/1990 | Fox, Jr. et al. ............. 424/618 |
| 4,960,413 A | 10/1990 | Sagar et al. |
| 5,019,096 A | 5/1991 | Fox, Jr. et al. |
| 5,064,413 A | 11/1991 | McKinnon et al. |
| 5,122,418 A | 6/1992 | Nakane et al. .............. 424/401 |
| 5,143,717 A | 9/1992 | Davis |
| 5,236,421 A | 8/1993 | Becher |
| 5,270,358 A | 12/1993 | Asmus |
| 5,312,335 A | 5/1994 | McKinnon et al. |
| D349,958 S | 8/1994 | Hollis et al. |
| 5,369,155 A | 11/1994 | Asmus |
| 5,372,589 A | 12/1994 | Davis |
| 5,383,851 A | 1/1995 | McKinnon, Jr. et al. |
| 5,399,163 A | 3/1995 | Peterson et al. |
| 5,454,886 A | 10/1995 | Burrell et al. .............. 148/565 |
| 5,454,889 A | 10/1995 | McNicol et al. |
| 5,457,015 A | 10/1995 | Boston |
| 5,520,639 A | 5/1996 | Peterson et al. |
| 5,534,288 A | 7/1996 | Gruskin et al. |
| 5,563,132 A | 10/1996 | Bodaness |
| 5,569,207 A | 10/1996 | Gisselberg et al. |
| 5,578,073 A | 11/1996 | Haimovich et al. |
| 5,631,066 A | 5/1997 | O'Brien |
| 5,681,575 A | 10/1997 | Burrell et al. |
| 5,744,151 A | 4/1998 | Capelli ....................... 424/405 |
| 5,753,251 A | 5/1998 | Burrell et al. |
| 5,770,255 A | 6/1998 | Burrell et al. .............. 427/2.1 |
| 5,770,258 A | 6/1998 | Takizawa |
| 5,792,793 A | 8/1998 | Oda et al. ................... 514/495 |

(Continued)

FOREIGN PATENT DOCUMENTS

CA 2242033 1/1999

(Continued)

OTHER PUBLICATIONS

Burrell, et al. "Efficacy of Silver-Coated Dressings as Bacterial Barriers in a Rodent Burn Sepsis Model" *Wounds* 1999; 11(4): 64-71.

(Continued)

*Primary Examiner*—John Pak
(74) *Attorney, Agent, or Firm*—Fish & Richardson P.C.

(57) ABSTRACT

The invention relates to the use of one or more antimicrobial metals selected from silver, gold, platinum, and palladium but most preferably silver, preferably formed with atomic disorder, and preferably in a nanocrystalline form, for the treatment of a acne. The nanocrystalline antimicrobial metal of choice may be used in the form of a nanocrystalline coating of one or more antimicrobial metals, a nanocrystalline powder of one or more antimicrobial metals, or a solution containing dissolved species from a nanocrystalline powder or coating of one or more antimicrobial metals.

20 Claims, No Drawings

U.S. PATENT DOCUMENTS

| | | | |
|---|---|---|---|
| 5,837,275 A | 11/1998 | Burrell et al. | |
| 5,848,995 A | 12/1998 | Walder | |
| 5,895,419 A | 4/1999 | Tweden et al. | |
| 5,899,880 A | 5/1999 | Bellhouse et al. | |
| 5,945,032 A | 8/1999 | Breitenbach et al. | 252/186.29 |
| 5,958,440 A | 9/1999 | Burrell et al. | |
| 5,981,822 A | 11/1999 | Addison | |
| 5,985,308 A | 11/1999 | Burrell et al. | |
| 6,010,478 A | 1/2000 | Bellhouse et al. | |
| 6,013,050 A | 1/2000 | Bellhouse et al. | |
| 6,017,553 A | 1/2000 | Burrell et al. | |
| 6,022,547 A | 2/2000 | Herb et al. | 424/401 |
| 6,071,541 A | 6/2000 | Murad | 424/616 |
| 6,071,543 A | 6/2000 | Thornfeldt | 424/642 |
| 6,096,002 A | 8/2000 | Landau | |
| 6,123,925 A | 9/2000 | Barry et al. | |
| 6,126,931 A | 10/2000 | Sawan et al. | 424/78.09 |
| 6,165,440 A | 12/2000 | Esenaliev | |
| 6,187,290 B1 | 2/2001 | Gilchrist et al. | |
| 6,197,351 B1 | 3/2001 | Neuwirth | |
| 6,201,164 B1 | 3/2001 | Wulff et al. | |
| 6,224,898 B1 | 5/2001 | Balogh et al. | 424/445 |
| 6,238,686 B1 | 5/2001 | Burrell et al. | |
| 6,258,385 B1 | 7/2001 | Antelman | 424/618 |
| 6,277,169 B1 | 8/2001 | Hampden-Smith et al. | |
| 6,294,186 B1 | 9/2001 | Beerse et al. | 424/405 |
| 6,333,093 B1 | 12/2001 | Burrell et al. | |
| 6,365,130 B1 | 4/2002 | Barry et al. | |
| 6,692,773 B1 * | 2/2004 | Burrell et al. | 424/618 |
| 6,720,006 B1 | 4/2004 | Hanke et al. | |
| 2001/0010016 A1 | 7/2001 | Modak et al. | |
| 2002/0001628 A1 | 1/2002 | Ito | |
| 2002/0016585 A1 | 2/2002 | Sachse | |
| 2002/0025344 A1 | 2/2002 | Newman et al. | 424/618 |
| 2002/0045049 A1 | 4/2002 | Madsen | |
| 2002/0051824 A1 | 5/2002 | Burrell et al. | |
| 2002/0192298 A1 | 12/2002 | Burrell et al. | |
| 2003/0054046 A1 * | 3/2003 | Burrell et al. | 424/618 |
| 2003/0194444 A1 | 10/2003 | Burrell et al. | |
| 2003/0203046 A1 | 10/2003 | Burrell et al. | |

FOREIGN PATENT DOCUMENTS

| | | |
|---|---|---|
| CN | 1082645 | 2/1994 |
| CN | 1241662 | 1/2000 |
| CN | 1262093 | 8/2000 |
| CN | 1279222 | 1/2001 |
| CN | 1291666 | 4/2001 |
| CN | 1291667 | 4/2001 |
| CN | 1306117 | 8/2001 |
| CN | 1322474 | 11/2001 |
| CN | 1322874 | 11/2001 |
| CN | 1328819 | 1/2002 |
| CN | 1328827 | 1/2002 |
| DE | 2748882 | 5/1979 |
| DE | 3807944 | 9/1989 |
| DE | 195 41 735 A1 | 5/1997 |
| EP | 0136768 A2 | 4/1985 |
| EP | 0 254 413 | 1/1988 |
| EP | 0 356 060 | 8/1989 |
| EP | 0355009 A1 | 2/1990 |
| EP | 0 378 147 | 7/1990 |
| EP | 0378147 A2 | 7/1990 |
| EP | 0599188 A1 | 6/1994 |
| EP | 0 681 841 A1 | 11/1995 |
| EP | 0681841 | 11/1995 |
| EP | 0780138 | 6/1997 |
| EP | 0 328 421 A2 | 8/1999 |
| EP | 1 159 972 | 12/2001 |
| GB | 420052 | 11/1934 |
| GB | 427106 | 4/1935 |
| GB | 965010 | 7/1964 |
| GB | 1270410 * | 4/1972 |
| GB | 2 073 024 | 10/1981 |
| GB | 2 140 684 | 12/1984 |
| HU | 980078 A | 9/1999 |
| IT | 022309 | 12/1990 |
| JP | 60-21912 | 2/1985 |
| JP | SHO 58-126910 | 2/1985 |
| JP | 04244029 A | 9/1992 |
| JP | 11 060493 | 3/1999 |
| JP | 11060493 | 3/1999 |
| JP | 11 116488 A | 4/1999 |
| JP | 11116488 | 4/1999 |
| JP | 11 124335 A | 5/1999 |
| JP | 11124335 | 5/1999 |
| JP | 2000 327578 A | 11/2000 |
| JP | 2000327578 | 11/2000 |
| WO | 87/07251 | 12/1987 |
| WO | WO 89/09054 | 10/1989 |
| WO | 92/13491 | 8/1992 |
| WO | 93/23092 | 11/1993 |
| WO | WO 93/23092 | 11/1993 |
| WO | 95/13704 | 5/1995 |
| WO | WO 95/13704 | 5/1995 |
| WO | WO 96/17595 | 6/1996 |
| WO | 98/41095 | 9/1998 |
| WO | WO 98/41095 | 9/1998 |
| WO | 98/51273 | 11/1998 |
| WO | 00/27390 | 5/2000 |
| WO | WO 00/27390 | 5/2000 |
| WO | 00/30697 | 6/2000 |
| WO | 00/44414 | 8/2000 |
| WO | 00/64505 | 11/2000 |
| WO | 00/64506 | 11/2000 |
| WO | WO 00/78281 | 12/2000 |
| WO | WO 00/78282 | 12/2000 |
| WO | 01/15710 | 3/2001 |
| WO | 01/24839 | 4/2001 |
| WO | 01/27365 | 4/2001 |
| WO | WO 01/26627 | 4/2001 |
| WO | 01/34686 | 5/2001 |
| WO | 01/41774 | 6/2001 |
| WO | 01/41819 | 6/2001 |
| WO | 01/43788 | 6/2001 |
| WO | 01/49301 | 7/2001 |
| WO | WO 01/49301 | 7/2001 |
| WO | WO 01/49302 | 7/2001 |
| WO | WO 01/49303 | 7/2001 |
| WO | 01/68179 A1 | 9/2001 |
| WO | 01/70052 | 9/2001 |
| WO | 01/74300 | 10/2001 |
| WO | WO 01/74300 | 10/2001 |
| WO | 01/80920 | 11/2001 |
| WO | SHO 01/49115 A1 | 12/2001 |
| WO | 02/09729 | 2/2002 |
| WO | 02/15698 | 2/2002 |
| WO | WO 02/09729 A2 | 2/2002 |
| WO | 02/18003 | 3/2002 |
| WO | WO 02/18699 | 3/2002 |
| WO | 02/44625 | 6/2002 |

OTHER PUBLICATIONS

Demling, et al., "The Role of Silver in Wound Healing: Effects of Silver on Wound Management," *Wounds*, vol. 13, No. 1, Jan./Feb. 2001 Supplement A; pp. 5-14.

Djokic et al., "An Electrochemical Analysis of Thin Silver Films Produced by Reactive Sputtering", *Journal of The Electrochemical Society*, 148 (3) C191-C196 (2001).

Kirsner et al., "The Role of Silver in Wound Healing Part 3: Matrix Metalloproteinsases in Normal and Impaired Wound Healing: A Potential Role of Nanocrystalline Silver",

*Wounds* vol. 13, No. 3, May/Jun. 2001, Supplement C, pp. 5-11.

Olson et al., "Healing of Porcine Donor sites Covered with Silver-coated Dressings"* *Eur J Surg* 2000; 166: 486-489.

Ovington, "The Role of Silver in Wound Healing: Why is Nanocrystalline Silver Superior? Nanocrystalline Silver: Where the Old and Familiar Meets a New Frontier," *Wounds*, vol. 13, No. 2, Mar./Apr. 2001, Supplement B; pp. 5-10.

Sant et al., "Novel duplex antimicrobial silver films deposited by magnetron sputtering", *Philosophical Magazine Letters*, 2000, vol. 80, No. 4, 249-256.

Tredget, "Evaluation of Wound Healing using Silver Dressing", Feb. 22, 1996.

Tredget et al., "A Matched-Pair, Randomized Study Evaluating the Efficacy and Safety of Acticoat* Silver-Coated Dressing for the Treatment of Burn Wounds," *Journal of Burn Care & Rehabilitation* Nov./Dec. 1998; 19:531-7.

Voigt, et al., "The Use of Acticoat as Silver Impregnated Telfa Dressings in a Regional Burn and Wound Care Center: The Clinicians View," *Wounds*, vol. 13, No. 2, Mar./Apr. 2001, Supplement B; pp. 11-20.

Wright et al., "Early healing events in a porcine model of contaminated wounds: effects of nanocrystalline silver on matrix metalloproteinases, cell apoptosis, and healing" *Wound Repair and Regeneration* 2002; 10:141-151.

Wright, et al., "The Comparative Efficacy of Two Antimicrobial Barrier Dressings: In-vitro Examination of Two Controlled Release of Silver Dressings" *Wounds* vol. 10, No. 6 Nov./Dec. 1998, pp. 179-188.

Wright, et al., "Efficacy of topical silver against fungal burn wound pathogens", *AJIC* vol. 27, No. 4, Aug. 1999.

Wright, et al., "Wound Management in an era of increasing bacterial antibiotic resistance: A role for topical silver treatment," *AJIC* vol. 26, No. 6; pp. 572-577 Dec. 1998.

Yin et al., "Comparative Evaluation of the Antimicrobial Activity of ACTICOAT* Antimicrobial Barrier Dressing" *Journal of Burn Care & Rehabilitation*, vol. 20, No. 3 May/Jun. 1999.

Yin, et al., "Effect of Acticoat Antimicrobial Barrier Dressing on Wound Healing and Graft Take", *Burn Care & Rehabilitation*, part 2 (Jan./Feb. 1999).

J. A. Thornton, "Influence of Apparatus Geometry and Deposition Conditions on the Structure and Topography of Thick Sputtered Coatings," J. Vac. Sci. Technol., vol. 11(4), 666-670, 1974.

Shigemasa et al., "Applications of Chitin and Chitosan for Biomaterials" *Biotechnology & Genetic Engineering Reviews* vol. 13 (14) pp. 383-420, date unavailable.

Thornton, "Deposition Technologies for Films and Coatings: Coating Deposition by Sputtering" *Materials Science Series* 5 pp. 170-243(1982).

Sant et al., "Morphology of Novel Antimicrobial Silver Films Deposited By Magnetron Sputtering" *Scripta Materiala*, vol. 41, No. 12, pp. 1333-1339, Nov. 19, 1999.

WPIDS abstract 1966-11488F (1966).

WPIDS abstract 1989-312257 (1989).

Medline abstract, accession No. 96064219 (1996).

Hoet, Peter H.M. et al., "Nanoparticles—known and unknown health risks," Journal of Nanobiotechnology, vol. 2, pp. 1-15, 2004.

Borm, Paul J. A. et al., "Toxicological hazards of inhaled nanoparticles—potential implications for drug delivery," Journal of Nanoscience and Nanotechnology, vol. 4(5), pp. 521-531, 2004.

Ozkan, M., "Quantum dots and other nanoparticles: what can they offer to drug discovery"? Drug Discovery Today, vol. 9(24), pp 1065-1071, 2004.

Williams, D., "Nanocrystalline metals: another opportunity for medical devices?" Medical Device Technology, vol. 14(9), p 12 (pp. 1-4 in the copy obtained via ProQuest), 2003.

Grier, N., Ph.D., "Silver Compounds and Its Compounds", Disinfection, Sterilization and Preservation, pp. 395-407, 1977. (S.S. Block, Lea and Febiger).

* cited by examiner

TREATMENT OF ACNE

FIELD OF THE INVENTION

The invention relates to the use of antimicrobial metals for the treatment of acne.

BACKGROUND OF THE INVENTION

Acne is a group of diseases whose initial pathology is the comedo and includes acne vulgaris, neonatal acne, infantile acne, and pomade acne. There are approximately 45 million people who suffer from acne in America alone. The disease is so common in youth at their puberty that it often has been termed physiological. Although acne stops appearing for most people by the age of 25, some people, the majority of them are women, experience the disease well into their adult life. This "adult acne" differs from teenage acne in location and that it tends to be more inflammatory with fewer comedones. It has received a great deal of attention recently.

Acne is a chronic inflammatory disease affecting the sebaceous glands. Acne lesions primarily involve the sebaceous glands located on the face, neck, chest and back. Both closed comedones (blackheads) and open comedones (whiteheads) are caused by hyperkeratinization of the infundibulum of the sebaceous duct. These keritinous plugs block the flow of sebum. These dilated ducts abound with the colonies of *Priopionibacterium acnes* and other fat splitting organisms. The clinically evident open and closed comedones and the microscopic microcomedo are the signal lesions of acne. The acne process results from a cascade of events. First, at puberty a spike in androgen production heralds an increase in sebum production and begins the hyperkeratinization process causing microcomedones and sebum blockade. With this blockage, the number of resident follicular flora increases dramatically. These bacteria produce inflammatory products, which permeate through thin walls of dilated sebum-filled duct. Once in the perifollicular dermis, they trigger the body's own immune defenses (both acute and granulaomatous) to produce the characteristic inflammatory papules, pustules and nodules characteristic of inflammatory acne.

The term "acne" is used herein as a general term to include inflammatory diseases of the pilosebaceous unit. In the medical field, the specific type of acne is usually indicated by a modifying term, although the term acne is frequently used alone to designate common acne or acne vulgaris.

There are four factors that are generally believed to be the contributors to the development of acne, any of which evidence "an acne problem area":
1. Increased sebum production;
2. Comedo formation, in which the follicular infundibulum hypercornifies, hyperkeratinizes, and hypodesquamates;
3. Colonization of the follicule by anaerobic *Propionibacterium*, mainly *P. acnes*; and
4. The host's inflammatory response.

These four factors are interrelated to each other. Sebum is comedogenic and causes inflammation by itself. The *Propionibacterium* has high lipolytic activity and liberates free fatty acids from sebum lipids. The free fatty acid has been shown to cause marked inflammation. The microorganisms also produce other extracellular enzymes such as proteases and hyaluronidases, and chemotactic factors, which may be important in the inflammatory process. Apart from these four factors, serum hormones, especially dehydroepiandrosterone sulfate, have been found to correlate with acne.

Acne commonly afflicts adolescents and young adults; however, there is growing number of patients who develop acne in their late twenties or thirties. There are data that suggest a familial or genetic tendency for patients to develop severe cystic or conglobate acne. Additionally, acne has been linked to endocrine disorders, especially those characterized by elevated levels of circulating testosterone or testosterone congeners. Exogenous agents that could exacerbate acne include medications e.g. iodides, anti-seisure, certain antibiotics and corticosteroids.

A number of dermatological disorders resemble acne having papules and pustules, but not comedones. These conditions represent follicular inflammation caused by drugs (androgens, lithium), bacteria, mechanical friction and unknown causes. Rosacea is the most common of these disorders and is receiving the most marketing attention with direct to consumer advertising by drug companies. This activity is directed toward the patients using topical metronidazole that appears to have anti-inflammatory activity. Treatment usually lasts 3 months.

Most acne treatments are directed at preventing inflammatory lesions, particularly the larger nodulo-cystic lesions that tend to be destructive and lead to permanent scarring. In general, visible comedones are the only minor cosmetic nuisances and do not lead to inflammatory lesions. Most acne treatment is directed to four arenas:
1. Keratinous plugs in sebaceous ducts;
2. Large sebaceous glands producing excess sebum;
3. Increased numbers of resident follicular bacteria; and
4. Inflammatory response to chemical mediators passing through the follicular wall.

Topical products used to remove comedones are known as comedolytics, the most effective being tretinoin, marketed as a prescription product (Retin A) and by several generic companies. Tretinoin or all-trans retinoic acid is the naturally occurring metabolite of Vitamin A. Tretinoin increases epidermal cell turnover, thus causing comedolysis and most importantly prevents the formation of new keratinous plugs. Applications of tretinoin is normally once a day at bedtime. Dryness, stinging and redness sometimes accompany the applications. Importantly, improvement is usually not seen for 6–8 weeks. Adapalene 0.1% (Differin) is a topical retinoid like tretinoin. Available by prescription only, the gel is usually applied once nightly. Side effects include frequent scaling, burning, redness and dryness. Improvement is delayed and is not evident for 4–8 weeks. Sodium sulfacetamide 10%/sulfur 5% (Sulfacet-R) is also available by prescription only. It is a lotion with antibacterial and comedolytic action. As with tretinoin, improvement is seen in 4–8 weeks. Salicylic acid 2% is an over the counter product that exhibits mild comedolytics activity.

The only products that have anti-sebum activity are estrogens and 13 cis-retinoic acid (isotretinoin) and these must be used systemically to be effective. Isotretinoin (Accutane) is a metabolite of Vitamin A available by prescription only. Isotretinoin is used to treat only severe cystic or conglobate acne. Because of its teratogenic properties, birth defects can occur. Isotretinoin is a powerful drug and can elevate triglycerides, total cholesterol and decrease high-density lipoproteins (HDL). Other side effects include dry skin, dry eyes, itching, headaches, nosebleed, and photosensitivity. It is generally taken for 4–5 months to see improvement. Recently, one brand of oral contraceptive has been approved for the treatment of acne for patients who request birth control.

A number of topical and systemic agents are used to lower the number of bacteria that colonize the follicular duct.

These include benzoyl peroxide (BP), BP 5%/erythromycin 3% (Benzamycin). BP has antibacterial activity and drying effects and is available over the counter or by prescription. BP is applied once or twice daily for 1–2 months. BP can produce erythema and peeling of skin. BP is often tried first for both non-inflammatory and mild inflammatory acne. Other topical antibiotics include clindamycin and erythromycin. These are used as solutions, lotions or gels by prescription only. Usually they are applied once or twice daily and results are seen in 1–2 months. Azelaic acid 20% (Azelex) also has mild antibacterial effects.

Systemic antibiotics include tetracycline and its analogs, which are used in low doses for years or until the end of the acne prone years. Most patients with mild inflammatory acne receive a combination of topical antibiotics and tretinoin or other retinoid. Bacterial resistance does occur so antibiotics may be changed or BP is substituted since resistance does not occur with BP. More severe acne requires systemic antibiotics and topical retinoid. The most severe must receive oral isotretinoin for 4–5 months.

There are no drugs that directly affect the inflammatory acne. The retinoids do have some anti-inflammatory properties, but these are poorly described. Topical steroid and even systemic steroids have been used to abort a severe flare of fulminant acne, but these are limited uses because of the side effects. Benzoyl peroxide gels are sometimes used as first aid on acne lesions. These function as a "drawing poultice", but data supporting this use is not available.

The treatment for acne centers around opening the pore, killing *P. acnes*, reducing sebum production and regulating inflammatory responses. Retinoids are the agents to reduce sebum production and open the pore. As a topical agent, Differin (adapalene) or Retin-A (tretinoin) is used for mild and moderate acne. Isotretinoin, an oral drug, is very effective but reserved for the severe and resistant acne because of its teratogenicity, hepatotoxicity, elevating triglyceride level and other side effects.

Topical and/or oral antimicrobial agents are commonly employed to treat acne. Topical benzoyl peroxide is used the most widely and is considered the best single topical agent. Tetracycline, Doxycycline and Minocycline are among the first line choices of oral antibiotics, in which Minocycline remains the premier drug for the treatment-resistant acne. Besides the side effects of the antimicrobial agents, development of resistant microorganisms has become an important issue nowadays. The number of patients harboring resistant *P. acnes* has been shown to be growing. While the patent literature reports that silver metal or silver salts such as silver nitrate, silver halides or silver sulphadiazine are amongst useful antibacterial agents for acne treatment, they have not, to the inventor's knowledge, been widely adopted for acne treatment.

Other approaches to acne include hormonal therapy with oral contraceptive pills as the major choice. It brings benefits to some patients over long term application. Intralesional corticosteroids and topical nicotinamide have also been used to control host's inflammatory response.

SUMMARY OF THE INVENTION

Through research, the inventors have established that crystalline anti-microbial metals such as silver, preferably formed with atomic disorder, are effective antimicrobial agents against the bacteria associated with acne. The inventors have further established through clinical observations with acne patients, and in animal experiments, that nanocrystalline anti-microbial metals such as silver, formed with atomic disorder, reduce the inflammatory reaction. This research has resulted in a new therapeutic treatment for acne. When the anti-microbial metal is silver, this new acne treatment will have advantages of fewer side effects and less chance of development of resistant bacteria.

The inventors have discovered that anti-microbial metals selected from one or more of silver, gold, platinum and palladium, are effective in the treatment of acne. These anti-microbial metals are formed with atomic disorder, such that ions, clusters, atoms or molecules of the metals are released at a concentration sufficient to provide a localized antimicrobial and anti-inflammatory effect. Most preferably, the antimicrobial metals are in a nanocrystalline form, and include sufficient atomic disorder to provide an antimicrobial and anti-inflammatory effect on a sustainable basis.

The crystalline forms of these antimicrobial metals may be used in any of the following formats:

i) coatings of the anti-microbial metals on medical grade substrates, for example, dressings, fibres, and materials composed of for example polyethylene, high density polyethylene, polyvinylchloride, latex, silicone, cotton, rayon, polyester, nylon, cellulose, acetate, carboxymethylcellulose, alginate, chitin, chitosan and hydrofibres;

ii) gels, formulated with nanocrystalline powders or solutions of the antimicrobial metals with such materials as carboxymethylcellulose, alginate, chitin, chitosar and hydrofibres, together with such ingredients as pectin and viscosity enhancers;

iii) creams, lotions, pastes and ointments formulated with nanocrystalline powders or solutions of the antimicrobial metals, for example as emulsions or with drying emollients;

iv) liquids, formulated as solutions by dissolving nanocrystalline coatings or powders of the antimicrobial metals, for example as topical solutions, aerosols or mists;

v) powders, preferably prepared as nanocrystalline powders of the antimicrobial metals, or as nanocrystalline coatings of the antimicrobial metals on biocompatible substrates in powder form, preferably on bioabsorbable and/or hygroscopic substrates such as:

Synthetic Bioabsorbable Polymers: for example polyesters/polyactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers, or Naturally Derived Polymers:

Proteins: albumin, fibrin, collagen, elastin;

Polysaccharides: chitosan, alginates, hyaluronic acid; and

Biosynthetic Polyesters: 3-hydroxybutyrate polymers.

In the above formats, the nanocrystalline antimicrobial metals are formulated from nanocrystalline coatings or nanocrystalline powders of the nanocrystalline antimicrobial metals, or from solutions prepared by dissolving the nanocrystalline coatings or powders therein. The formulations include a therapeutically effective amount of the coatings or powders, and most preferably, the following amounts:

| | |
|---|---|
| For coatings: | 150–3000 nm thick coatings |
| For gels, creams and lotions: | 0.01–5% by weight of the nanocrystalline antimicrobial metal powder |
| For liquids | 0.001–1% by weight of the antimicrobial metal |

Nanocrystalline coatings of the antimicrobial metals are most preferably deposited onto one or more layers of medical dressing materials which can be laminated with uncoated layers of medical dressing materials. The coatings can be prepared by known techniques for preparing nanocrystalline coatings, but are most preferably prepared by physical vapour deposition under conditions which create atomic disorder. The nanocrystalline coatings may be prepared to create an interference colour so as to provide an indicator, as described in prior patent application WO 98/41095, published Sep. 24, 1998, and naming inventors R. E. Burrell and R. J. Precht.

Nanocrystalline powders of the antimicrobial metals may be prepared as nanocrystalline coatings, preferably of the above thickness, on powdered substrates such as chitin, or may be prepared as nanocrystalline coatings on a substrate such as a silicon wafer, and then scraped off as a nanocrystalline powder. Alternatively, fine grained or nanocrystalline powders of the antimicrobial metals may be cold worked to impart atomic disorder, as disclosed in prior patent application WO 93/23092, published Nov. 25, 1993, naming Burrell et al., as inventors.

As used herein and in the claims, the terms and phrases set out below have the meanings which follow.

"Metal" or "metals" includes one or more metals whether in the form of substantially pure metals, alloys or compounds such as oxides, nitrides, borides, sulphides, halides or hydrides.

"Antimicrobial metals" are silver, gold, platinum and palladium, or mixtures of such metals with same or other metals, with silver metal being the most preferred.

"Biocompatible" means generating no significant undesirable host response for the intended utility. Most preferably, biocompatible materials are non-toxic for the intended utility. Thus, for human utility, biocompatible is most preferably non-toxic to humans or human tissues.

"Sustained release" or "sustainable basis" are used to define release of atoms, molecules, ions or clusters of a antimicrobial metal that continues over time measured in hours or days, and thus distinguishes release of such metal species from the bulk metal, which release such species at a rate and concentration which is too low to be therapeutically effective, and from highly soluble salts of antimicrobial metals such as silver nitrate, which releases silver ions virtually instantly, but not continuously, in contact with an alcohol or electrolyte.

"Atomic disorder" includes high concentrations of: point defects in a crystal lattice, vacancies, line defects such as dislocations, interstitial atoms, amorphous regions, grain and sub grain boundaries and the like relative to its normal ordered crystalline state. Atomic disorder leads to irregularities in surface topography and inhomogeneities in the structure on a nanometer scale.

"Normal ordered crystalline state" means the crystallinity normally found in bulk metal materials, alloys or compounds formed as cast, wrought or plated metal products. Such materials contain only low concentrations of such atomic defects as vacancies, grain boundaries and dislocations.

"Diffusion", when used to describe conditions which limit diffusion in processes to create and retain atomic disorder, i.e. which freeze-in atomic disorder, means diffusion of atoms (adatom diffusion) and/or molecules on the surface or in the matrix of the material being formed.

"Alcohol or water-based electrolyte" is meant to include any alcohol or water-based electrolyte that the anti-microbial materials of the present invention might contact in order to activate (i.e. cause the release of species of the antimicrobial metal) into same. The term is meant to include alcohols, water, gels, fluids, solvents, and tissues containing water, including body fluids (for example blood, urine or saliva), and body tissue (for example skin, muscle or bone).

"Bioabsorbable" as used herein in association includes substrates which are useful in medical devices, that is which are biocompatible, and which are capable of bioabsorption in period of time ranging from hours to years, depending on the particular application.

"Bioabsorption" means the disappearance of materials from their initial application site in the body (human or mammalian) with or without degradation of the dispersed polymer molecules.

"Colour change" is meant to include changes of intensity of light under monochromatic light as well as changes of hue from white light containing more than one wavelength.

An "interference colour" is produced when light impinges on two or more partly reflective surfaces separated by a distance which bears the right relationship to the wavelength of the light to be removed by destructive interference.

"Partly reflective" when used to describe the base or top layer materials, means that the material has a surface which reflects a portion of incident light, but which also transmits a portion of the incident light. Reflection occurs when a ray of incoming light encounters a boundary or interface characterized by a change in refractive index between two media. For the top layer of the anti-microbial materials of this invention, that interface is with air. For the base layer, the interface is with the top layer. The reflectance of the base and top layers is balanced so as to generate an interference colour.

"Partly light transmissive" when used to describe a thin film of the top layer material means that the thin film is capable of transmitting at least a portion of incident visible light through the thin film.

"Detectable" when used to describe a colour change means an observable shift in the dominant wavelength of the reflected light, whether the change is detected by instrument, such as a spectrophotometer, or by the human eye. The dominant wavelength is the wavelength responsible for the colour being observed.

"Cold working" as used herein indicates that the material has been mechanically worked such as by milling, grinding, hammering, mortar and pestle or compressing, at temperatures lower than the recrystallization temperature of the material. This ensures that atomic disorder imparted through working is retained in the material.

"Therapeutically effective amount" is used herein to denote any amount of a formulation of the nanocrystalline antimicrobial metals which will exhibit an anti-microbial and an anti-inflammatory effect in acne when applied to the affected area. A single application of the formulations of the present invention may be sufficient, or the formulations may be applied repeatedly over a period of time, such as several times a day for a period of days or weeks. The amount of the active ingredient, that is the antimicrobial metal in the form of a coating, powder or dissolved in liquid solution, will vary with the conditions being treated, the stage of advancement of the condition, and the type and concentration of the formulation being applied. Appropriate amounts in any given instance will be readily apparent to those skilled in the art or capable of determination by routine experimentation.

"Nanocrystalline" is used herein to denote single-phase or multi-phase polycrystals, the grain size of which is less than about 100, more preferably <50 and most preferably <25 nanometers in at least one dimension. The term, as applied to the crystallite or grain size in the crystal lattice of coatings, powders or flakes of the antimicrobial metals, is not meant to restrict the particle size of the materials when used in a powder form.

"Powder" is used herein to include particulate sizes of the nanocrystalline antimicrobial metals ranging from nanocrystalline powders to flakes. Most preferably, powders of the present invention are sized at less than 100 µm, and more preferably less than 40 µm.

"Grain size", or "crystallite size" means the size of the largest dimension of the crystals in the antimicrobial metal coating or powder.

DESCRIPTION OF THE PREFERRED EMBODIMENTS

Crystalline forms of the antimicrobial metals Ag, Au, Pt, and Pd can be prepared as powders or coatings, or as solutions prepared by dissolving the coatings or powders. The crystalline coatings or powders are most preferably formed with atomic disorder in accordance with the techniques published in the prior patent applications of Burrell et al., see for example WO 93/23092, published Nov. 25, 1993, WO 95/13704, published May 26, 1995 and WO 98/41095, published Sep. 24, 1998.

A. Antimicrobial Metal Coatings on Dressings

Dressings carrying nanocrystalline coatings of antimicrobial metals in accordance with the invention include at least one, and possibly more layers of medical dressing materials. Multiple layers may be laminated together by known means such as low temperature thermal fusing, stitching or, most preferably, ultrasonic welding.

The dressing may be formed to include an occlusive or semi-occlusive layer such as an adhesive tape or polyurethane film in order to secure the dressing in place, and retain moisture for release of ions, atoms, molecules or clusters of the antimicrobial metal (hereinafter antimicrobial metal species).

The preferred and alternate compositions of the dressing layers, together with the preferred nanocrystalline antimicrobial metal coatings, are set out in further detail below.

I) Dressing Materials

The dressing is formed of a perforated, preferably non-adherent material which allows for fluids to penetrate or diffuse there through in either or both directions. The perforated material may be formed of a woven or non-woven, non-woven being preferred, fabric such as cotton, gauze, a polymeric net or mesh such as polyethylene, nylon, polypropylene or polyester, an elastomer such as polyurethane or polybutadiene elastomers, or a foam such as open cell polyurethane foam. Exemplary perforated, non-adherent materials useful for the dressing include non-woven meshes such as DELNET™ P530, which is a non-woven veil formed of high density polyethylene using extrusion, embossing and orientation processes, produced by Applied Extrusion Technologies, Inc. Of Middletown, Del., USA. This same product is available as Exu-Dry CONFORMANT 2™ Wound Veil, from Frass Survival Systems, Inc., Bronx, New York, USA as a subset of that company's Wound Dressing Roll (Non-Adherent) products. Other useful non-woven meshes include CARELLE™ or NYLON 90™, available from Carolina Formed Fabrics Corp., N-TERFACE™, available from Winfield Laboratories, Inc., of Richardson, Tex., USA. Exemplary woven meshes may be formed from fibreglass or acetate, or cotton gauze. An exemplary hydrophilic polyurethane foam is HYPOL™, available from W.R. Grace & Co., New York, N.Y., USA.

For ease of ultrasonic welding for lamination, at least one dressing layer is preferably formed from a polymeric material which is amenable to ultrasonic welding, that is which will melt on the application of localized heat and then fuse multiple layers together on cooling.

If desired, a second, absorbent layer is formed from an absorbent material for holding sufficient moisture next to the skin in order to activate the antimicrobial metal coating, that is to cause release of ions, molecules, atoms or clusters of the antimicrobial metal in order to cause an anti-microbial and anti-inflammatory effect. Preferably, the absorbent material is an absorbent needle punched non-woven rayon/polyester core such as SONTARA™ 8411, a 70/30 rayon/polyester blend commercially available from Dupont Canada, Mississauga, Ontario, Canada. This product is sold by National Patent Medical as an American White Cross sterile gauze pad. However, other suitable absorbent materials include woven or non-woven materials, non-woven being preferred made from fibers such as rayon, polyester, rayon/polyester, polyester/cotton, cotton and cellulosic fibers. Exemplary are creped cellulose wadding, an air felt of air laid pulp fibers, cotton, gauze, and other well known absorbent materials suitable for medical dressings.

A third layer of the dressing, if used, is preferably formed of perforated, non-adherent material such as used in the first layer. This allows moisture penetration as sterile water and the like are added in order to activate the antimicrobial metal coating.

Additional layers may be included between or above the first, second and third layers as is well known in medical dressings. The coated dressing layers may be combined with an adhesive layer, in a well known manner.

The dressing may be used as a single layer, or may be used as multiple layers laminated together at intermittent spaced locations across the dressing by ultrasonic welds. Ultrasonic welding is a known technique in the quilting art. Briefly, heat (generated ultrasonically) and pressure are applied to either side of the dressing at localized spots through an ultrasonic horn so as to cause flowing of at least one of the plastic materials in the first and second layers and the subsequent bonding together of the layers on cooling. The welds appear at localized circular spots and are preferably less than 0.5 cm in diameter.

The use of ultrasonic welding of the layers at spaced locations has the advantage of retaining the absorbent and moisture penetration properties of the dressing layers, while retaining the conforming properties of the dressing. Edge seams, stitching and adhesives have the disadvantage of interfering with one or more of these desirable properties of the dressings. Furthermore, by spacing the welds at intermittent locations across the dressing, the dressing may be cut to smaller sizes, as needed, without causing delamination. Preferred spacings of about 2.5 cm between welds allows the dressing to be cut down to about 2.5 cm sizes, while maintaining at least one weld to hold the laminated layers together.

ii) Nanocrystalline Coatings of Antimicrobial Metals

The dressing preferably includes a nanocrystalline coating of one or more of the antimicrobial metals. The coating is applied to one or more of the dressing layers, but is most preferably applied at least to the skin facing layer.

The nanocrystalline coating is most preferably formed with atomic disorder in accordance with the procedures set out above and as described in WO 93/23092, WO 95/13704, and WO98/41095, and as set out below. Most preferably, the coating is formed as a multilayer coating of the antimicrobial metals, having a top and a base layer, as set below, to produce an interference colour. In this way, the coating provides not only the active ingredient for the treatment of acne, but also acts as an indicator of activation of the dressing. As the top layer of the coating is activated with an alcohol or water-based electrolyte, such as sterile water or ethanol, even minor dissolution of the antimicrobial metal results in a detectable colour change, indicating that the coating has been activated. If there is no colour change, additional moisture might be provided to the dressing by adding water, until a colour change is detected. Once activated, the dressing should be maintained in a moist condition, for example by the addition of sterile water, if necessary.

iii) Sterilization

Dressings with nanocrystalline coatings of a antimicrobial metal formed with atomic disorder are preferably sterilized without applying excessive thermal energy, which can anneal out the atomic disorder, thereby reducing or eliminating a useful release of antimicrobial metal species. Gamma radiation is preferred for sterilizing such dressings, as discussed in WO 95/13704. Electron beam and ethylene oxide sterilization techniques can also be used.

It should be appreciated that the use of ultrasonic welding to laminate the layers of dressings with nanocrystalline coatings formed from antimicrobial metals with atomic disorder is advantageous since it achieves bonding in localized spots and avoids applying heat to any significant portion of the dressing, thereby avoiding any significant reduction in the solubility of the antimicrobial metals through annealing out of the atomic disorder.

The sterilized dressings should be sealed in packaging which excludes light penetration to avoid additional oxidation of the antimicrobial metal coating. Polyester peelable pouches are preferred. The shelf life of dressings thus sealed is over one year.

iv) Directions for Use of Dressings for Acne

The dressing is placed on the affected portion of the skin and is moistened with drops of sterile water or, for example 70% ethanol, in order to activate the coating for release of antimicrobial metal species. The dressing is then secured in place with an occlusive or semi-occlusive layer, such as an adhesive tape or polyurethane film, which keeps the dressing in a moist environment.

As set out in Examples 5, dressings carrying a bi-layer nanocrystalline antimicrobial metal coating formed with silver having atomic disorder, manufactured as set out above and as described in greater detail in Example 1, have shown substantial clinical response in treating acne. Dressings prepared with a single layer of silver having a reduced content of oxygen in the coating, as set forth in Example 2, gave similar clinical results, without staining the skin. In use, the dressings are kept moist, at 100% relative humidity. Adding sterile water initially to activate the antimicrobial metal coating is needed, and then as needed to maintain the dressing in a moist condition. Dressings may be changed as required for observation and cleaning. Preferably dressings are changed daily, but could be left longer, such as 3 days, and can provide a therapeutic effect for a much longer period of time.

v) Multilayer Nanocrystalline Coatings of Antimicrobial Metals With Interference Colour The dressings preferably include the antimicrobial metal coating formed with at least two metal layers, a base layer and a top layer over the base layer, so as to produce an interference colour, as set forth in WO 98/41095. Both layers are partly reflective; the top layer is partly light transmissive. The top layer is a thin film containing at least one antimicrobial metal formed with sufficient atomic disorder such that the top layer, in contact with an alcohol or water based electrolyte, releases ions, atoms, molecules or clusters of the antimicrobial metal, at a concentration sufficient to provide a therapeutic effect, on a sustainable basis. In this way, the top layer, in contact with the alcohol or electrolyte, will undergo a change in optical path length, either by a change in thickness resulting from some dissolution, or through a change in the refractive index of the top layer resulting from a change in the composition of a newly formed thin layer formed on the top layer. Either or both of these results are sufficient to cause a detectable colour change, thus providing an indicator that the top layer has been activated.

Both the base layer and the top layer are formed from a partly reflective material. In this way, at least a portion of the incoming light is reflected from the surface of the layer while another portion is transmitted through the layer. The top layer is partly light transmissive to allow incident light to reach the interface with the base layer. The top layer thus cannot approximate 100% reflectivity, such as in pure Al or Ag, or interference colours cannot be generated, as is well known in the art. The materials for the top and base layers should be balanced in their reflectances in order to generate an interference colour. Generally, the top layer is deposited as a thin film having a thickness which maintains adequate transmittance to generate an interference colour. Furthermore, the refractive index for the materials in layers is different, accomplished by differences in their actual or effective compositions. For instance different materials in the two layers will result in the materials having different actual refractive indexes. However, if it is desired to make the layers from the same material, the layers can be deposited with different porosities or different levels/types of atomic disorder, in order to achieve different effective compositions, and thus different refractive indexes.

In this manner, incoming light reflects off the interface of the base and top layers. Incoming light reflects from the interface of the top layer with air, and interferes with the light reflected from the interface with the base layer so as to generate an "interference colour". The particular colour which is generated and its brightness will depend on the properties of the layers, most importantly on the composition of the layers, which determines its transmittance and absorption properties, along with its refractive index, and on the thickness of the layers. Generally, it is desirable to generate first and second order interference colours, by limiting the thickness of the base layer and top layers to minimize the number of internal reflections. First and second order interference colours are generally brighter than third and fourth order etc. colours, making them more aesthetically pleasing, more consistently reproducible in manufacturing, and more susceptible to detectable colour change on variations in thickness on dissolution of even aminor amount of the top layer.

The property which determines the particular colour which is generated is the effective optical thickness of the top layer, that is the product of the refractive index of the top layer material and the actual thickness of the top layer. Thus the colour which is desired can be altered by changing the actual thickness or the top layer or its refractive index.

Preferably, the material in the base layer is a reflective metal. Such metals are known in the art and include, for example one or more of the valve metals; e.g. Ta, Nb, Ti, Zr and Hf, as well as transition metals such as Au, Ag, Pt, Pd, Sn, Cu, V, W and Mo, or the metal Al. More preferably, the base layer is formed from one or more of the antimicrobial metals Ag, Au, Pt, and Pd, most preferably Ag, in a partly reflective form.

The base layer may be formed by known techniques, such as the vapour deposition techniques of evaporation or physical vapour deposition. Preferably, the base layer is formed as a thin film by physical vapour deposition with atomic disorder, as set out below and in WO 95/13704, in order to produce a sustainable release of the antimicrobial metal species when the base layer is ultimately exposed to an alcohol or water based electrolyte. The thickness of the base layer is generally not critical, provided that it is partly reflective. Preferred thicknesses will vary widely with the material composition. However, in that the layer is preferably a thin film formed by physical vapour deposition techniques, it should be at least about 25 nm thick to create a useful colour. The base layer should be greater than 60 nm thick, more preferably 300 to 2500 nm thick, and most preferably 600 to 900 nm thick.

The top layer is formed of a partly reflective, partly light transmissive thin film containing at least one antimicrobial metal, most preferably Ag, formed with atomic disorder so as to produce a sustainable release of the antimicrobial metal species, and ultimate colour change, when exposed to an alcohol or a water based electrolyte. The thickness of the top layer formed from these metals is preferably less than 400 nm in order to maintain the preferred level of light transmission. The desired thickness will vary with the composition of the top layer, and with the desired end colour and colour change. For first and second order interference colours, the thickness will generally be less than about 400 nm. More preferably, the thickness will range from 5 to 210 nm, most preferably from 10 to 100 nm.

The top layer may be a thin film of the base layer material, formed with a different refractive index for instance by altering the deposition conditions to change the porosity, composition and/or degree of atomic disorder in the layers.

When the base layer is itself formed from a antimicrobial metal with atomic disorder, the top layer may be provided as an in situ generated top layer by virtue of its thickness and/or composition changing on contacting an alcohol or water based electrolyte, so as to produce an interference colour which differs from the initial colour of the base layer.

Most preferably, the top layer is a thin film of a composite material formed by co-, sequentially or reactively depositing a antimicrobial metal in a matrix with atoms or molecules of a different material to create atomic disorder in the matrix, in the manner set out below. The different material is selected from a) biocompatible metals, b) oxygen, nitrogen, hydrogen, boron, sulphur or halogens, or c) an oxide, nitride, carbide, boride, halide, sulphide or hydride of either or both of a antimicrobial metal or a biocompatible metal. Most preferably, the top layer material is a composite material containing silver, and one or both of silver oxide and atoms or molecules containing oxygen trapped or absorbed in the silver matrix. The term "silver oxide" is meant to include any oxide or mixture of oxides of silver. However, the top layer is preferably not formed solely of AgO and/or $Ag_2O$, since the solubility of these materials is low.

vi) Nanocrystalline Coatings of Antimicrobial Metals Containing Atomic Disorder

At least the top layer, and preferably also the base layer, is formed in a crystalline form from one or more antimicrobial metals with atomic disorder. The production of atomic disorder through physical vapour deposition techniques is described in WO 93/23092 and WO 95/13704, and as outlined below.

The antimicrobial metal is deposited as a thin metallic film on one or more surfaces of the dressing by vapour deposition techniques. Physical vapour techniques, which are well known in the art, all deposit the metal from the vapour, generally atom by atom, onto a substrate surface. The techniques include vacuum or arc evaporation, sputtering, magnetron sputtering and ion plating. The deposition is conducted in a manner to create atomic disorder in the coating as defined above. Various conditions responsible for producing atomic disorder are useful. These conditions are generally those which one has been taught to avoid in thin film deposition techniques, since the object of most thin film depositions is to create a defect free, smooth and dense film (see for example J. A. Thornton, "Influence of Apparatus Geometry and Deposition Conditions on the Structure and Topography of Thick Sputtered Coatings," J. Vac. Sci. Technol., 11(4), 666–670, 1974).

The preferred conditions which are used to create atomic disorder during the deposition process include:

a low substrate temperature, that is maintaining the surface to be coated at a temperature such that the ratio of the substrate temperature to the melting point of the metal (in degrees Kelvin) is less than about 0.5, more preferably less than about 0.35 and most preferably less than about 0.3; and optionally one or both of:

a higher than normal working (or ambient) gas pressure, i.e. for vacuum evaporation: e-beam or arc evaporation, greater than 0.001 Pa (0.01 mT), gas scattering evaporation (pressure plating) or reactive arc evaporation, greater than 2.67 Pa (20 mT); for sputtering: greater than 10 Pa (75 mT); for magnetron sputtering: greater than about 1.33 Pa (10 mT); and for ion plating: greater than about 26.67 Pa (200 mT); and maintaining the angle of incidence of the coating flux on the surface to be coated at less than about 75°, and preferably less than about 30°.

For economic reasons, the thin metal film has a thickness no greater than that needed to provide release of antimicrobial metal species on a sustainable basis over a suitable period of time, and to generate the desired interference colour. Within the preferred ranges of thicknesses set out above, the thickness will vary with the particular metal in the coating (which varies the solubility and abrasion resistance), and with the degree of atomic disorder in (and thus the solubility of) the coating. The thickness will be thin enough that the coating does not interfere with the dimensional tolerances or flexibility of the device for its intended utility.

The therapeutic effect of the material so produced is achieved when the coating is brought into contact with an alcohol or a water based electrolyte, thus releasing metal ions, atoms, molecules or clusters. The concentration of the metal species which is needed to produce a therapeutic effect will vary from metal to metal.

The ability to achieve release of metal atoms, ions, molecules or clusters on a sustainable basis from a coating is dictated by a number of factors, including coating characteristics such as composition, structure, solubility and thickness, and the nature of the environment in which the device is used. As the level of atomic disorder is increased, the amount of metal species released per unit time increases. For instance, a silver metal film deposited by magnetron sputtering at T/Tm<0.5 and a working gas pressure of about 0.93 Pa (7 mT) releases approximately ⅓ of the silver ions that a film deposited under similar conditions, but at 4 Pa (30 mT), will release over 10 days. Films that are created with an intermediate structure (ex. lower pressure, lower angle of incidence etc.) have Ag release values intermediate to these values as determined by bioassays. This then provides a method for producing controlled release metallic coatings. Slow release coatings are prepared such that the degree of disorder is low while fast release coatings are prepared such that the degree of disorder is high.

For continuous, uniform coatings, the time required for total dissolution will be a function of film thickness and the nature of the environment to which they are exposed. The relationship in respect of thickness is approximately linear, i.e. a two fold increase in film thickness will result in about a two fold increase in longevity.

It is also possible to control the metal release from a coating by forming a thin film coating with a modulated structure. For instance, a coating deposited by magnetron sputtering such that the working gas pressure was low (ex. 2 Pa or 15 mT) for 50% of the deposition time and high (ex. 4 Pa or 30 mTorr) for the remaining time, has a rapid initial release of metal ions, followed by a longer period of slow release. This type of coating is extremely effective on devices such as urinary catheters for which an initial rapid release is required to achieve immediate anti-microbial concentrations followed by a lower release rate to sustain the concentration of metal ions over a period of weeks.

The substrate temperature used during vapour deposition should not be so low that annealing or recrystallization of the coating takes place as the coating warms to ambient temperatures or the temperatures at which it is to be used (ex. body temperature). This allowable $\Delta T$, that the temperature differential between the substrate temperature during deposition and the ultimate temperature of use, will vary from metal to metal. For the most preferred metal, Ag, preferred substrate temperatures of $-20$ to $200°$ C., more preferably $-10°$ C. to $100°$ C. are used.

Atomic order may also be achieved, in either or both of the base and top layers by preparing composite metal materials, that is materials which contain one or more antimicrobial metals in a metal matrix which includes atoms or molecules different from the antimicrobial metals.

The preferred technique for preparing a composite material is to co- or sequentially deposit the antimicrobial metal(s) with one or more other inert, biocompatible metals selected from Ta, Ti, Nb, Zn, V, Hf, Mo, Si, Al and alloys of these metals or other metal elements, typically other transition metals. Such inert metals have a different atomic radii from that of the antimicrobial metals, which results in atomic disorder during deposition. Alloys of this kind can also serve to reduce atomic diffusion and thus stabilize the disordered structure. Thin film deposition equipment with multiple targets for the placement of each of the antimicrobial and biocompatible metals is preferably utilized. When layers are sequentially deposited the layer(s) of the biocompatible metal(s) should be discontinuous, for example as islands within the antimicrobial metal matrix. The final weight ratio of the antimicrobial metal(s) to biocompatible metal(s) should be greater than about 0.2. The most preferable biocompatible metals are Ti, Ta, Zn and Nb. It is also possible to form the anti-microbial coating from oxides, carbides, nitrides, sulphides, borides, halides or hydrides of one or more of the antimicrobial metals and/or one or more of the biocompatible metals to achieve the desired atomic disorder.

Another composite material may be formed by reactively co- or sequentially depositing, by physical vapour techniques, a reacted material into the thin film of the antimicrobial metal(s). The reacted material is an oxide, nitride, carbide, boride, sulphide, hydride or halide of the antimicrobial and/or biocompatible metal, formed in situ by injecting the appropriate reactants, or gases containing same, (ex. air, oxygen, water, nitrogen, hydrogen, boron, sulphur, halogens) into the deposition chamber. Atoms or molecules of these gases may also become absorbed or trapped in the metal film to create atomic disorder. The reactant may be continuously supplied during deposition for codeposition or it may be pulsed to provide for sequential deposition. The final weight ratio of reaction product to antimicrobial metal(s) should be greater than about 0.05. Air, oxygen, nitrogen and hydrogen are particularly preferred reactants, with oxygen being most preferred.

The above deposition techniques to prepare composite coatings may be used with or without the conditions of lower substrate temperatures, high working gas pressures and low angles of incidence previously discussed. One or more of these conditions are preferred to retain and enhance the amount of atomic disorder created in the coating.

B. Powders of Antimicrobial Metals

Powders of one or more antimicrobial metals formed with atomic disorder, most preferably in a nanocrystalline form, may be prepared either as pure metals, metal alloys or compounds such as metal oxides or metal salts, by vapour deposition, mechanical working, or compressing to impart atomic disorder, as set out below, or by the procedures set out in WO 93/23092, WO 95/13704, or as otherwise known in the art. Mechanically imparted disorder is conducted by milling, grinding, hammering, mortar and pestle or compressing, under conditions of low temperature (i.e., temperatures less than the temperature of recrystallization of the material) to ensure that annealing or recrystallization does not take place. Nanocrystalline powders may be prepared by preparing nanocrystalline coatings in the manner set out above, onto a substrate such as a cold finger or a silicon wafer, and then scraping off the coating to form a powder. Alternatively, nanocrystalline coatings such as set out above may be formed onto powdered substrates which are biocompatible. Particularly preferred substrates are bioabsorbable and/or hygroscopic powders such as chitin. Exemplary bioabsorbable and/or hygroscopic powders are composed of:

Synthetic Bioabsorbable Polymers: for example polyesters/polyactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers.

Naturally Derived Polymers:

Proteins: albumin, fibrin, collagen, elastin;

Polysaccharides: chitosan, alginates, hyaluronic acid; and

Biosynthetic Polyesters: 3-hydroxybutyrate polymers.

Most preferably, powders of the present invention are sized at less than 100 $\mu$m, and more preferably less than 40 $\mu$m.

The prepared nanocrystalline powders may then be incorporated into or onto medical dressings or pharmaceutical formulations, by any methods known in the art. For example, the powders may be layered onto the substrates (dressings or powders), mechanically mixed within the fibres of the dressings, impregnated into dressings by physical blowing, or added to topical pharmaceutical composition ingredients.

The antimicrobial and anti-inflammatory effects of the nanocrystalline powder is achieved when the powder is brought into contact with an alcohol or a water-based electrolyte, thus releasing the antimicrobial metal ions, atoms, molecules or clusters.

Nanocrystalline powders may be sterilized as described above.

C. Formulations and Dosages

Typically, the nanocrystalline antimicrobial metals will be formulated from the active ingredient, namely nanocrystalline powders or coatings of the antimicrobial metals, or dissolved species from such powders or coatings, in the form of:

coatings on medical dressings or biocompatible powdered substrates, powders included in medical dressings, topical pharmaceutical compositions such as gels, pastes, ointments, creams, lotions, emulsions, suspensions or powders, liquid pharmaceutical compositions prepared by dissolving nanocrystalline coatings or powders of the antimicrobial metals in pharmaceutically acceptable carriers such as water, for application in drop, mist or aerosol forms.

In the pharmaceutical compositions, the amount of the nanocrystalline metal powder may range broadly from about 0.001% to about 30% by weight, but will more preferably fall in the range of from about 0.01 to 5% by weight. Coatings of the nanocrystalline antimicrobial metals may be very thin, or thicker, depending on the desired duration of application on the patient. Typical coating thicknesses are in the range of 150 to 3000 nm thick. As liquid formulations, the amount of dissolved antimicrobial metal will typically range between about 0.001 to 1% by weight.

Besides the active ingredient, pharmaceutical compositions may also include non-toxic, pharmaceutically and dermatologically acceptable carriers, diluents and excipients, suitable for topical application, as are well known, see for example Merck Index, Merck & Co., Rahway, N.J., Bioreversible Carriers in Drug Design, Theory and Application, Roche (ed.) Pergamon Press, (1987), Gilman et al., (eds) (1990) Goodman and Gilman's: The Pharmacological Bases of Therapeutics, $8^{th}$ Ed., Pergamon Press; Novel Drug Delivery Systems, $2^{nd}$ Ed., Norris (ed.) Marcel Dekker Inc., (1989), and Remington's Pharmaceutical Sciences. For standard dosages of conventional pharmacological agents, see, e.g., Physicians Desk Reference (1997 Edition); and American Medical Association (1997) Drug Evaluations (Subscriptions).

Dosage forms for the topical administration of compositions of the nanocrystalline antimicrobial metals include various mixtures and combinations that can be applied topically and will permit even spreading and absorption into the cutaneous surfaces. Examples include sprays, mists, aerosols, lotions, creams, solutions, gels, ointments, pastes, emulsions, and suspensions. The active compound can be mixed under sterile conditions with a pharmaceutically acceptable carrier, and with any preservatives, buffers, or propellants which may be required. Topical preparations can be prepared by combining the antimicrobial metal powder with conventional pharmaceutically acceptable diluents and carriers commonly used in topical dry, liquid, cream and aerosol formulations. Ointment and creams can, for example, be formulated with an aqueous or oily base with the addition of suitable thickening and/or gelling agents. An exemplary base is water. Thickening agents which can be used according to the nature of the base include aluminum stearate, cetostearyl alcohol, propylene glycol, polyethey-lene glycols, hydrogenated lanolin, and the like. Lotions can be formulated with an aqueous base and will, in general, also include one or more of the following: stabilizing agents, emulsifying agents, dispersing agents, suspending agents, thickening agents, coloring agents, perfumes, and the like. Powders can be formed with the aid of any suitable powder base, e.g., talc, lactose starch and the like. Drops can be formulated with an aqueous base or non-aqueous base, and can also include one or more dispersing agents, suspending agents, solubilizing agents, and the like.

Ointments, pastes, creams and gels also can contain excipients, such as starch, tragacanth, cellulose derivatives, polyethylene glycols, silicones, bentonites, silicic acid, and talc, or mixtures thereof. Powders and sprays also can contain excipients such as lactose, talc, silicic acid, aluminum hydroxide, calcium silicates and polyamide powder, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such a chlorofluorohydrocarbons and volatile unsubstituted hydrocarbons, such as butane and propane.

Multiple inactive ingredients are generally incorporated in topical formulations to improve cosmetic acceptability, and are optional ingredients in the formulations. Examples of ingredients are emulsifiers, emollients, thickening agents, solvents, colouring agents, anti-foaming agents, preservatives, fragrances, and fillers may also be added, as is well known in the art.

The dosage of the active ingredients depends upon many factors that are well known to those skilled in the art, for example, the particular form of the active ingredient, the condition being treated, the age, weight, and clinical condition of the recipient patient, and the experience and judgement of the clinician or practitioner administering the therapy. A therapeutically effective amount of the nanocrystalline antimicrobial metal is that which provides either subjective relief of symptoms or an objectively identifiable improvement as noted by the clinician or other qualified observer. The dosing range varies with the metal used, its form, the route of administration and the potency of the particular compound.

D. Methods of Treating Acne

The invention provides methods of treating acne, by administering a therapeutically effective amount of a nanocrystalline antimicrobial metal powder, or a solution derived from a nanocrystalline antimicrobial metal, as either a topical formulation, or as a coating on medical dressing, applied to the locally affected skin area. A therapeutically effective amount may be determined by testing formulations containing the nanocrystalline antimicrobial metals by in vitro or in vivo testing. Topical applications may be applied one or more times a day. Dressings coated with the nanocrystalline antimicrobial metals may be changed daily, or even less frequently, and should be kept in a moist condition with the addition of saline, alcohols, or more preferably sterile water, in order to release ions, atoms, molecules or clusters of the nanocrystalline metal, on a sustained basis.

E. Examples

Example 1

Preparation of Nanocrystalline Silver Coatings on Dressings

This example shows the preparation of a bilayer nanocrystalline silver coating on a dressing material. A high density polyethylene dressing, DELNET™ or CONFORMANT 2™ was coated with a silver base layer and a silver/oxide top layer to generate a coloured anti-microbial coating having indicator value. The coating layers were formed by magnetron sputtering under the conditions set out in Table 1.

TABLE 1

| Sputtering Conditions: | Base Layer | Top Layer |
|---|---|---|
| Target | 99.99% Ag | 99.99% Ag |
| Target Size | 20.3 cm diameter | 20.3 cm diameter |
| Working Gas | 96/4 wt % Ar/$O_2$ | 96/4 wt % Ar/$O_2$ |
| Working Gas Pressure | 5.33 Pa (40 mT) | 5.33 Pa (40 mT) |
| Power | 0.3 kW | 0.15 kW |
| Substrate Temperature | 20° C. | 20° C. |
| Base Pressure | $3.0 \times 10^{-6}$ Torr | $3.0 \times 10^{-6}$ Torr |
| Anode/Cathode Distance | 100 mm | 100 mm |
| Sputtering Time | 7.5–9 min | 1.5 min |
| Voltage | 369–373 V | 346 V |

The resulting coating was blue in appearance. A fingertip touch was sufficient to cause a colour change to yellow. The base layer was about 900 nm thick, while the top layer was 100 nm thick.

To establish that silver species were released from the coated dressings, a zone of inhibition test was conducted. Mueller Hinton agar was dispensed into Petri dishes. The agar plates were allowed to surface dry prior to being inoculated with a lawn of *Staphylococcus aureus* ATCC No. 25923. The inoculant was prepared from Bactrol Discs (Difco, M.), which were reconstituted as per the manufacturer's directions. Immediately after inoculation, the coated materials to be tested were placed on the surface of the agar. The dishes were incubated for 24 hr. at 37° C. After this incubation period, the zone of inhibition was calculated (corrected zone of inhibition=zone of inhibition−diameter of the test material in contact with the agar). The results showed a corrected ZOI of about 10 mm, demonstrating good release of silver species.

The coating was analyzed by nitric acid digestion and atomic absorption analysis to contain 0.24+/−0.04 mg silver per mg high density polyethylene. The coating was a binary alloy of silver (>97%) and oxygen with negligible contaminants, based on secondary ion mass spectroscopy. The coating, as viewed by SEM, was highly porous and consisted of equiaxed nanocrystals organized into coarse columnar structures with an average grain size of 10 nm. Silver release studies in water demonstrated that silver was released continuously from the coating until an equilibrium concentration of about 66 mg/L was reached (determined by atomic absorption), a level that is 50 to 100 times higher than is expected from bulk silver metal (solubility$\leq$1 mg/L).

By varying the coating conditions for the top layer to lengthen the sputtering time to 2 min, 15 sec., a yellow coating was produced. The top layer had a thickness of about 140 nm and went through a colour change to purple with a fingertip touch. Similarly, a purple coating was produced by shortening the sputtering time to 1 min, to achieve a top layer thickness of about 65 nm. A fingertip touch caused a colour change to yellow.

To form a three layer dressing, two layers of this coated dressing material were placed above and below an absorbent core material formed from needle punched rayon/polyester (SONTARA™ 8411). With the silver coating on both the first and third layers, the dressing may be used with either the blue coating side or the silver side in the skin facing position. For indicator value, it might be preferable to have the blue coating visible. The three layers were laminated together by ultasonic welding to produce welds between all three layers spaced at about 2.5 cm intervals across the dressing. This allowed the dressing to be cut down to about 2.5 cm size portions for smaller dressing needs while still providing at least one weld in the dressing portion.

The coated dressings were sterilized using gamma radiation and a sterilization dose of 25 kGy. The finished dressing was packaged individually in sealed polyester peelable pouches, and has shown a shelf life greater than 1 year in this form. The coated dressings can be cut in ready to use sizes, such as 5.1×10.2 cm strips, before packaging. Alternatively, the dressings may be packaged with instructions for the patient or clinician to cut the dressing to size.

Additional silver coated dressings were prepared in a full scale roll coater under conditions to provide coatings having the same properties set out above, as follows:

the dressing material included a first layer of silver coated DELNET, as set out above, laminated to STRATEX, AET, 8.0NP$_2$-A/QW, which is a layer of 100% rayon on a polyurethane film.

Silver Foam Dressing—three layers of silver coated high density polyethylene prepared as above, alternating with two layers of polyurethane foam, L-00562-6 Medical Foam, available from Rynel Ltd., Bootbay, Me., USA.

Example 2

Preparation of Nanocrystalline Silver Coating on HDPE Mesh

The silver coated mesh was produced, as set forth in Example 1, by sputtering silver onto Delnet, a HDPE mesh (Applied Extrusion Technologies, Inc., Middletown, Del., USA) using Westaim Biomedical TMRC unit under the following conditions:

TABLE 2

| Sputtering conditions | |
|---|---|
| Target: | 99.99% Ag |
| Target Size: | 15.24 cm × 152.4 cm |
| Working Gas: | 99.375:0.625 wt % Ar/$O_2$ |
| Working Gas Pressure: | 5.33 Pa (40 mTorr) |
| Total Current: | 22 A |
| Base Pressure: | $5.0 \times 10^{-5}$ Torr |
| Web Speed: | 577 mm/min |
| Voltage: | 367 V |

The coating was tested and found to have a weight ratio of reaction product to silver of between 0.05 and 0.1. The dressing was non-staining to human skin.

Example 3

Preparation of Nanocrystalline Silver Powders

Nanocrystalline silver powder was prepared by sputtering silver coatings on silicon wafers using Westaim Biomedical NGRC unit, and then scraping the coating off. The sputtering conditions were as follows:

TABLE 3

| Sputtering Conditions | |
|---|---|
| Target: | 99.99% Ag |
| Target Size: | 15.24 cm × 1216.125 cm |
| Working Gas: | 75:25 wt % Ar/$O_2$ |
| Working Gas Pressure: | 40 mTorr |
| Total Current: | 40 A |
| Base Pressure: | $5.0 \times 10^{-5}$ Torr |
| Sandvik Belt Speed: | 340 mm/min |
| Voltage: | 370 V |

The powder has a particle size ranging from 2 µm to 100 µm, with crystallite size of 8 to 10 nm, and demonstrated a positive rest potential.

Example 4

In vitro Activity of Silver Solution against *Propionibacterium acne*

An in vitro test was conducted to determine if silver solutions according to the present invention effectively control *Propionibacterium acne*. The silver solution was obtained by static elution of Acticoat™ Burn Wound Dressing (lot #: 00403A-05, Westaim Biomedical Corp., Fort Saskatchewan, Canada) with nanopure water in a ratio of one square inch of dressing in five milliliters of water for 24 hours at room temperature. The silver concentration of the silver solution was determined by an atomic absorption method. The silver elute was diluted with nanopure water to 20 µg/ml. The *Propionibacterium acne* (ATCC No. 0919) was provided by Biofilm Research Group, University of Calgary.

The inoculum was prepared by inoculating freshly autoclaved and cooled tubes of Tryptic soy broth (TSB) with *P.acnes* and incubating them for 2 days at 37° C. in an anaerobic jar. At this time, the optical density of the suspensions was 0.3 at a wavelength of 625 nm.

The bacterial suspension (100 µL) was mixed with 100 µL of the silver solution being tested. The final concentration of silver in these mixtures was 10 µg/ml. The mixtures were incubated in an anaerobic jar at 37° C. for two hours. The silver was neutralized by addition of 0.4% STS (0.85%NaCl, 0.4% Sodium thioglycolate, 1% Tween 20) and the solution was serially 10-fold diluted with phosphate-buffered saline. 20 µL aliquots of the original solution and subsequent dilutions were plated onto TSA drop plates. The drops were allowed to dry and the plates were incubated in an anaerobic jar at 37° C. for 72 hours at which time the colonies were counted. The control consisted of 100 µL of bacterial suspension mixed with 100 µL of nanopure water and treated as above.

The results showed that the silver solution according to the present invention, at a final concentration of 10 µg/ml, gave 4.3 logarithm reduction in viable *Propionibacterium acne* counts in two hours.

Example 5

Treatment of Acne

A sixteen year old female was diagnosed with acne vulgaris. She had numerous red papules and pustules on her forehead. Various skin cleansing regimes and antibiotic (erythromycin and clindomycin) treatments had been tried and had failed to control the acne. Prior to bed time, the papules and pustules on one side of her forehead were moistened and covered with a nanocrystalline silver coated high density polyethylene mesh, prepared as in Example 1 (single layer, blue coating). The mesh was then occluded with a thin film dressing which remained in place for 10 hours. Upon removal the papules and pustules were no longer red and were only slightly raised. Some brown staining of the skin was observed.

Example 6

Treatment of Acne

A sixteen year old male was diagnosed with acne vulgaris. He had numerous raised, red papules and pustules on his forehead. Various skin cleansing regimes and antibiotic treatments had been tried and had failed to control the acne. The patient was placed on isotretinoin treatment which controlled his acne well. He did develop a single large pustule on his forehead which was embarassing for him. Prior to bed time, the pustule was moistened and covered with a nanocrystalline silver coated high density polyethylene mesh prepared as in Example 2.. The mesh was then occluded with a thin film dressing which remained in place for 10 hours. Upon removal the pustule was no longer red and was only slightly raised. A second treatment resulted in the disappearance of the pustule.

Example 7

Treatment of Acne

A sixteen year old female was diagnosed with acne vulgaris. She had numerous red papules and pustules on her forehead. Various skin cleansing regimes and antibiotic (erythromycin and clindomycin) treatments had been tried and had failed to control the acne. Prior to bed time, the papules and pustules on one side of her forehead were moistened and covered with a nanocrystalline silver coated high density polyethylene mesh, prepared as in Example 2. The mesh was then occluded with a thin film dressing which remained in place for 10 hours. Upon removal the papules and pustules were no longer red and were only slightly raised. A second treatment resulted in the disappearance of the papules and virtual elimination of the pustules.

The silver coated mesh, when prepared as set forth in Example 2, did not result in any staining of the skin.

All publications mentioned in this specification are indicative of the level of skill of those skilled in the art to which this invention pertains. All publications are herein incorporated by reference to the same extent as if each individual publication was specifically and individually indicated to be incorporated by reference.

The terms and expressions in this specification are, unless otherwise specifically defined herein, used as terms of description and not of limitation. There is no intention, in using such terms and expressions, of excluding equivalents of the features illustrated and described, it being recognized that the scope of the invention is defined and limited only by the claims which follow.

We claim:

1. A method of treating acne conditions, the method comprising:
   contacting an acne problem area of a patient with a therapeutically effective amount of one or more antimicrobial metals in a nanocrystalline form to provide a localized antimicrobial and anti-inflammatory effect, wherein:
   the one or more antimicrobial metals in nanocrystalline form have sufficient atomic disorder so that the one or more antimicrobial metals in nanocrystalline form, when in contact with an alcohol or water-based electrolyte, releases atoms, ions, molecules, or clusters of the one or more antimicrobial metals in nanocrystalline form into the alcohol or water-based electrolyte on a sustainable basis and at a concentration sufficient to provide a localized antimicrobial and anti-inflammatory effect; and
   the one or more antimicrobial metals are provided as a coating on, or filler in, a dressing, or in a pharmaceutical composition with one or more pharmaceutically and dermatologically acceptable carriers, diluents or excipients suitable for topical administration.

2. The method as set forth in claim 1, wherein the antimicrobial metal is nanocrystalline silver, wherein nanocrystalline indicates a grain size which is less than 100 nanometers in at least one dimension.

3. The method as set forth in claim 1, wherein the pharmaceutical composition includes a nanocrystalline powder of said one or more antimicrobial metals, or a solution containing dissolved species from a nanocrystalline powder or coating of said one or more antimicrobial metals.

4. The method as set forth in claim 3, wherein the pharmaceutical composition is a gel, cream or lotion containing the antimicrobial metal powder in an amount of 0.01–5% by weight, or a liquid containing 0.001–1% by weight of the antimicrobial metal.

5. The method as set forth in claim 1, wherein the coating is provided on a dressing.

6. The method as set forth in claim 5, wherein the coating is 15–3000 nm thick.

7. The method as set forth in claim 5, wherein the coating comprises:
   a base layer of partly reflective material capable of generating an interference color when covered with a partly reflective, partly light transmissive top layer; and
   a top layer formed over said base layer, said top layer being a partly reflective, partly light transmissive thin film containing at least one noble metal in nanocrystalline form and having a thickness so that a first or second order interference color is produced, said top layer having a refractive index different from that of said base layer, and the noble metal being formed with sufficient atomic disorder so that the top layer, in contact with an alcohol or water based electrolyte, releases ions, atoms, molecules or clusters of the noble metal into the alcohol or water based electrolyte on a sustainable basis.

8. The method as set forth in claim 7, wherein the dressing is fixed in place with an occlusive or semi-occlusive layer which maintains the dressing in a moist condition.

9. The method as set forth in claim 8, wherein the occlusive layer or semi-occlusive layer is an adhesive tape or film.

10. The method as set forth in claim 2, wherein the antimicrobial metal is nanocrystalline silver, wherein nanocrystalline indicates a grain size which is less than 50 nanometers in at least one dimension.

11. The method as set forth in claim 10, wherein the antimicrobial metal is nanocrystalline silver, wherein nanocrystalline indicates a grain size which is less than 25 nanometers in at least one dimension.

12. The method as set forth in claim 3, wherein the nanocrystalline powder includes particulates of the one or more antimicrobial metals having a particulate size which is less than 100 $\mu$m.

13. The method as set forth in claim 12, wherein the nanocrystalline powder includes particulates of the one or more antimicrobial metals having a particulate size which is less than 40 $\mu$m.

14. A method of treating acne conditions, comprising:
   contacting an acne problem area of a patient with a therapeutically effective amount of a pharmaceutical composition to provide a localized antimicrobial and anti-inflammatory effect,
   wherein:
   the pharmaceutical composition comprises:
     an antimicrobial metal in a nanocrystalline form; and
     one or more pharmaceutically and dermatologically acceptable carriers, diluents or excipients suitable for topical administration; and
   the antimicrobial metal in nanocrystalline form has sufficient atomic disorder so that the antimicrobial metal in nanocrystalline form, when in contact with an alcohol or water-based electrolyte, releases atoms, ions, molecules, or clusters of the metal into the alcohol or water-based electrolyte on a sustainable basis and at a concentration sufficient to provide a localized antimicrobial and anti-inflammatory effect.

15. The method as set forth in claim 14, wherein the pharmaceutical composition comprises a gel, cream or lotion containing the antimicrobial silver in a nanocrystalline form in an amount of 0.01 to 5% by weight.

16. The method as set forth in claim 14, wherein the antimicrobial metal in nanocrystalline form has a grain size of less than 100 nanometers in at least one dimension.

17. The method as set forth in claim 14, wherein the antimicrobial metal in nanocrystalline form has a grain size of less than 50 nanometers in at least one dimension.

18. The method as set forth in claim 14, wherein the antimicrobial metal in nanocrystalline form has a grain size of less than 25 nanometers in at least one dimension.

19. The method of claim 14, wherein the antimicrobial metal in nanocrystalline form is selected from the group consisting of antimicrobial silver in nanocrystalline form, antimicrobial gold in nanocrystalline form, antimicrobial platinum in nanocrystalline form, and antimicrobial palladium in nanocrystalline form.

20. The method according to claim 14, wherein the antimicrobial metal in nanocrystalline form comprises antimicrobial silver in nanocrystalline form.

* * * * *